(12) United States Patent
Melkent et al.

(10) Patent No.: US 8,123,809 B2
(45) Date of Patent: Feb. 28, 2012

(54) DEPLOYMENT SYSTEM AND METHOD FOR AN EXPANDABLE VERTEBRAL IMPLANT

(75) Inventors: Anthony J. Melkent, Memphis, TN (US); Keith E. Miller, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 345 days.

(21) Appl. No.: 12/424,666

(22) Filed: Apr. 16, 2009

(65) Prior Publication Data

US 2010/0268338 A1 Oct. 21, 2010

(51) Int. Cl.
*A61F 2/44* (2006.01)
(52) U.S. Cl. .................. 623/17.15; 623/17.11
(58) Field of Classification Search .... 623/17.11–17.13, 623/17.15; 606/90, 105
See application file for complete search history.

(56) References Cited

U.S. PATENT DOCUMENTS

| | | | |
|---|---|---|---|
| 4,554,914 A | 11/1985 | Kapp et al. | |
| 4,932,975 A | 6/1990 | Main et al. | |
| 5,123,926 A | 6/1992 | Pisharodi | |
| 6,375,682 B1 | 4/2002 | Fleischmann et al. | |
| 6,454,806 B1 | 9/2002 | Cohen et al. | |
| 6,719,796 B2 | 4/2004 | Cohen et al. | |
| 7,547,325 B2 | 6/2009 | Biedermann et al. | |
| 2001/0032020 A1* | 10/2001 | Besselink .................. 623/17.15 | |
| 2002/0161444 A1 | 10/2002 | Chio | |
| 2004/0172129 A1 | 9/2004 | Schafer | |
| 2004/0199252 A1 | 10/2004 | Sears et al. | |
| 2004/0249461 A1 | 12/2004 | Ferree | |
| 2006/0241762 A1 | 10/2006 | Kraus | |
| 2007/0073397 A1* | 3/2007 | McKinley .................. 623/17.11 |
| 2008/0021556 A1 | 1/2008 | Edie | |
| 2008/0058931 A1 | 3/2008 | White et al. | |
| 2009/0048676 A1 | 2/2009 | Fabian | |

FOREIGN PATENT DOCUMENTS

| | | |
|---|---|---|
| DE | 4416605 C1 | 6/1995 |
| DE | 10344019 B3 * | 5/2005 |
| WO | 02071986 A2 | 9/2002 |
| WO | 03013399 A1 | 2/2003 |
| WO | 2008144175 A1 | 11/2008 |

OTHER PUBLICATIONS

Translation of DE 10344019 B3.*
Steinmetz, Management of Metastatic Tumors of the Spine: Strategies and Operative Indications, Neurosurg Focus 11(6), 2001, © 2001 American Association of Neurological Surgeons, pp. 1-9.
Errico, A New Method of Thoracic and Lumbar Body Replacement for Spinal Tumors: Technical Note, ISSN: 0148-396X, Accession: 00006123-199304000-00030, vol. 32(4), Apr. 1993, p. 678-681, Copyright © by the Congress of Neurological Surgeons, Departments of Orthopedics and Neurosurgery, New York University Medical Center, New York, NY.

* cited by examiner

*Primary Examiner* — Thomas J Sweet
*Assistant Examiner* — Megan Wolf

(57) ABSTRACT

Embodiments of the invention include expandable implants incorporated into a system for deploying the expandable implants to replace skeletal structures such as one or more vertebrae or portions of the spine or vertebrae. Some embodiments include related methods of implanting devices using deployment systems.

13 Claims, 6 Drawing Sheets

US 8,123,809 B2

DEPLOYMENT SYSTEM AND METHOD FOR AN EXPANDABLE VERTEBRAL IMPLANT

FIELD OF THE INVENTION

The present invention relates generally to the field of replacing portions of the human structural anatomy with medical implants, and more particularly relates to an expandable implant incorporated into a system for deploying the expandable implant to replace skeletal structures such as one or more vertebrae or portions of the spine or vertebrae.

BACKGROUND

Expandable medical implants are often useful at least because the implants may be introduced into a surgical site with a reduced profile that facilitates reduced disruption of surrounding tissues. Expandable medical implants may be useful in at least some spinal fusion procedures and in at least some vertebral body replacement procedures. Spinal fusion procedures are often effective to restore proper vertebral spacing and relieve pressure on nerves and consequent pain. Also, it is sometimes necessary to remove one or more vertebrae, or a portion of the vertebrae, from the human spine in response to various pathologies. For example, one or more of the vertebrae may become damaged as a result of tumor growth, or may become damaged by a traumatic or other event. Removal, or excision, of a vertebra may be referred to as a vertebrectomy. Excision of a generally anterior portion, or vertebral body, of the vertebra may be referred to as a corpectomy. An implant is usually placed between the remaining vertebrae to provide structural support for the spine as a part of a corpectomy or vertebrectomy. This may generally be referred to as vertebral body replacement.

Many prior art devices have deployed expandable medical implants with the aid of relatively large or complex insertion, expansion, distraction, and retraction instruments. Some devices require a significant incision and retraction of tissue to enable controlled expansion of the implant. A smaller incision may be particularly useful with a posterior approach to the spine. To effectively make a posterior approach, an implant may be placed through a window created between a nerve root, the spinal cord, and an extent of an excised vertebra. The nerve root may be mobilized to increase the size of the window slightly, but excess movement may risk damage to the nerve root. Therefore, for a posterior approach, an initially small expandable implant may have particular utility. A posterior approach may be preferred for patients with circumferential tumors or for patients more susceptible to the risks associated with a more extensive anterior approach. Similarly, initially small implants enabling minimal tissue disruption may be useful from any surgical approach to reduce trauma to surrounding tissues and to enhance patient recovery. Likewise, a deployment mechanism that does not require tissue disruption beyond the disruption required to introduce an implant is advantageous.

Connections between bones and implants may also be useful in replacing bones or portions of joints or appendages such as the legs and arms, or other bones. Examples include, but are not limited to, a femur, tibia, fibula, humerus, radius, ulna, phalanges, clavicle, and any of the ribs. Use of the mechanisms described and claimed herein are equally applicable to treatment or repair of such bones or appendages.

SUMMARY

One embodiment of the invention is a system for deploying an expandable medical implant. The expandable medical implant may include a base and an expandable end and an enclosed volume between the base and the expandable end. The expandable medical implant may also include an elongated member with a distal end and a proximal end. The distal end is coupled to the expandable end of the expandable medical implant, and the elongated member is in contact with the base of the expandable medical implant to provide a connection between the expandable end and the base. The proximal end extends from the expandable implant and the proximal end is configured to receive a force applied along its length.

An embodiment of the invention is a method of implanting an expandable medical implant. The method may include providing an expandable medical implant with a base and an expandable end and an enclosed volume between the base and the expandable end, and an elongated member with a distal end and a proximal end wherein the distal end is coupled to the expandable end of the expandable medical implant and the elongated member is in contact with the base of the expandable medical implant. The method may also include introducing the expandable medical implant through an incision in a patient, and applying a compressive force to the elongated member to push apart the base and the expandable end of the expandable medical implant.

Another embodiment of the invention is a method of implanting an expandable medical implant. The method may include providing an expandable medical implant with a base and an expandable end and an enclosed volume between the base and the expandable end, and an elongated member with a distal end and a proximal end. The distal end is coupled to the expandable end the expandable medical implant and the elongated member are in contact with the base of the expandable medical implant. The method may also include applying a tensile force to the elongated member to pull together the base and the expandable end of the expandable medical implant, introducing the expandable medical implant through an incision in a patient, and releasing the tensile force applied to the elongated member to allow the base and the expandable end of the expandable medical implant to separate.

DETAILED DESCRIPTION

Figure 1:
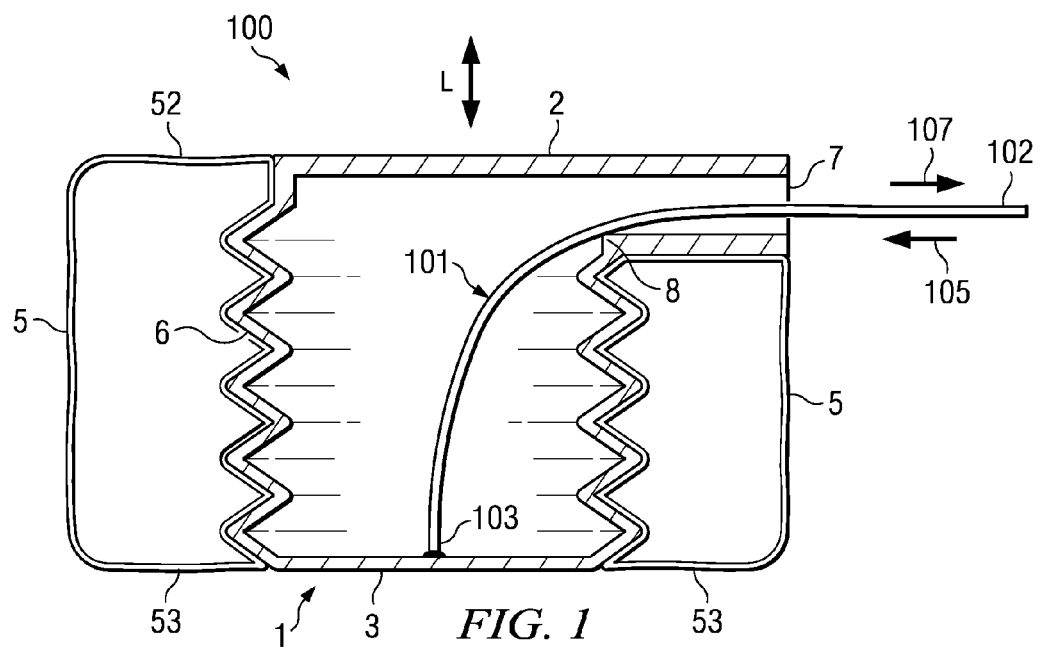
FIG. 1 is a cross-sectional view of an embodiment of a system for deploying an expandable medical implant.
Figure 2:
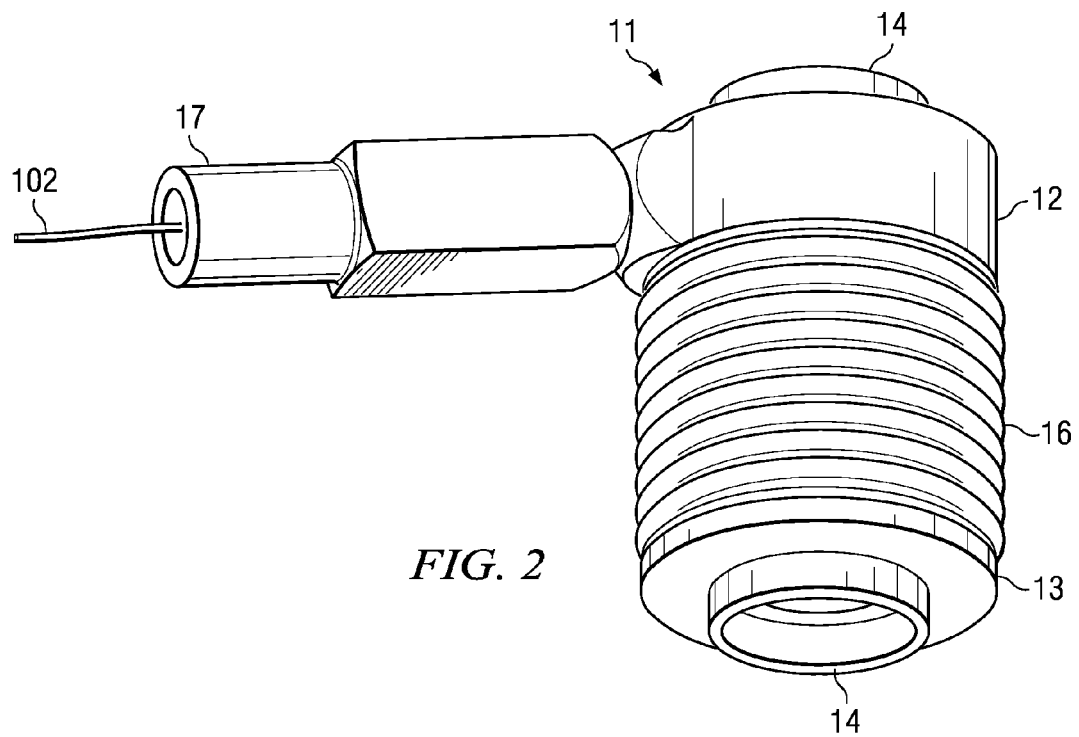
FIG. 2 is a perspective view of at least a portion of an expandable medical implant in an unexpanded state.

FIG. 1 illustrates a system 100 for deploying an expandable medical implant 1. The expandable medical implant 1 includes a base 2 and an expandable end 3. The illustrated expandable medical implant 1 includes a membrane 5 and an expansion mechanism 6. The expansion mechanism 6 shown in FIG. 1 is a bellows. The expansion mechanism of other embodiments may be, without limitation, a combination of nested, telescoping cylinders, as illustrated in FIGS. 6-9, a ratchet mechanism, a threaded or partially threaded mechanism, or any other mechanism that may drive or hold expansion of an expandable medical implant.

The membrane 5 is illustrated in a partially expanded configuration in FIG. 1. The membrane 5 of some embodiments is configured to be placed between vertebrae and expanded such that an upper surface 52 contacts a first vertebra and an opposite lower surface 53 contacts a second vertebra to provide support between the vertebrae. The longitudinal axis, or linear expansion direction L, of the expandable medical implant 1 is illustrated in FIG. 1. Lateral expansion of the membrane 5 is also accomplished in some embodiments. As used herein, the term lateral means directions approximately normal to the linear expansion direction L.

The membrane 5 may be constructed, in whole or in part, of a non-permeable material. The membrane 5 may include compliant or non-compliant balloon materials such as those commonly used to manufacture coronary and Kyphoplasty medical devices. Such materials may include, but are not limited to, mylar, rubber, polyurethane, vinyl, latex, polyethylenes, ionomer, and polytetrapthalate (PET), as well as less flexible materials such as Kevlar®, PEBAX®, stainless steel, titanium, nickel-titanium alloys, and other metals and alloys and/or ceramics. A compliant membrane may include reinforcing to limit one or both of the size and shape of the membrane to a clinically advantageous extent. A non-compliant membrane may expand more elastically to more completely fill an irregular opening, depending on the amount of material introduced into the membrane.

Likewise the membrane 5 may be constructed, in whole or in part, of a permeable material, which allows a certain amount of a fill material to pass through the membrane 5. All or a portion may be made permeable by fabricating a material, including but not limited to, the membrane materials listed above, into a fabric, weave, mesh, composite, bonded fiber assembly, or any other manufacture known to those skilled in the art. For example, all or part of the upper surface 52 and the opposite lower surface 53 may be constructed of a permeable material to allow fill material to move through the membrane 5 and to come into contact with vertebrae.

In the embodiment shown in FIG. 1, the expansion mechanism 6 defines an enclosed volume, and the membrane 5 defines an enclosed volume that incorporates the enclosed volume of the expansion mechanism 6. The enclosed volumes of both the expansion mechanism 6 and the membrane 5 are therefore volumes between the base 2 and the expandable end 3.

The system 100 for deploying an expandable medical implant 1 shown in FIG. 1 includes an elongated member 101 with a distal end 103 and a proximal end 102. The illustrated distal end 103 is coupled to the expandable end 3 of the expandable medical implant 1. The elongated member 101 is in contact with the base 2 of the expandable medical implant 1 at a point 8 to provide a connection between the expandable end 3 and the base 2. The proximal end 102 extends from the expandable implant 1 in FIG. 1 through an opening or port 7. The illustrated connection between the expandable end 3 and the base 2 with the elongated member 101 is a sliding connection because the elongated member 101 slides relative to the base 2 when the elongated member is removed from or pushed into the port 7.

The proximal end 102 is configured to receive a force applied along its length. Arrow 105 shows the direction of a pushing or compressive force applied along the length of the elongated member 101 at its proximal end 102. Arrow 107 shows the direction of a pulling or tensile force applied along the length of the elongated member 101 at its proximal end 102. In other embodiments where the elongated member 101 is actuated by an alternative mechanism, the force applied to the elongated member 101 may be a twisting, winding, turning, or other effective force to push apart or pull together the base 2 and the expandable end 3. For example, and without limitation, the elongated member 101 may include threaded portions, turnbuckle portions, fasteners, or multiple members that move relative to one another to lengthen or shorten the elongated member 101. In some embodiments, the elongated member 101 is a wire, rod, or other relatively rigid device that is capable of transmitting both tensile and compressive forces to either or both pull together or push apart the base 2 and the expandable end 3. In other embodiments where it is only necessary to pull together the base 2 and the expandable end 3, the elongated member 101 may be a strand, string, rope, cable, or other member configured primarily to transmit tensile forces.

In some embodiments, elasticity in the material of the expansion mechanism 6 may serve as a biasing force to bias the expansion mechanism 6 toward an expanded or unexpanded state, as may be advantageous in various circumstances. For example, it may be advantageous to bias the expansion mechanism 6 toward an unexpanded state to provide a low profile device for insertion. Other devices, such as but not limit to the elongated member 101, or a fluid injected through the port 7, may be used to expand the expansion mechanism 6. A fluid that drives linear expansion of the expandable medical implant 1 or maintains linear expansion of the expandable medical implant 1 may be introduced through the port 7. The fluid may be merely for expansion and retention, or may be a component of a fill material intended to remain in the expansion mechanism 6. As used in association with this function, a fluid may be a paste, gel, liquid, suspension, granular mixture, or similar substance. A substance as described herein will be considered a fluid even if it later cures or hardens to a non-fluidic state. Both the expansion mechanism 6 and the membrane 5 may be initially unexpanded linearly. The port 7 may also be used to handle the expandable medical implant 1 or to guide the implant into a position where it can be effectively deployed.

In other circumstances, it may be preferred to bias the expansion mechanism 6 toward an expanded state. With such an embodiment, another component, such as but not limit to the elongated member 101, may be used to keep the expansion mechanism 6 in an unexpanded state while the expandable medical implant 1 is inserted. Following insertion, the expansion mechanism 6 may be released and allowed to increase toward its expanded state by releasing the elongated member 101 relative to the base 2.

Figure 3:
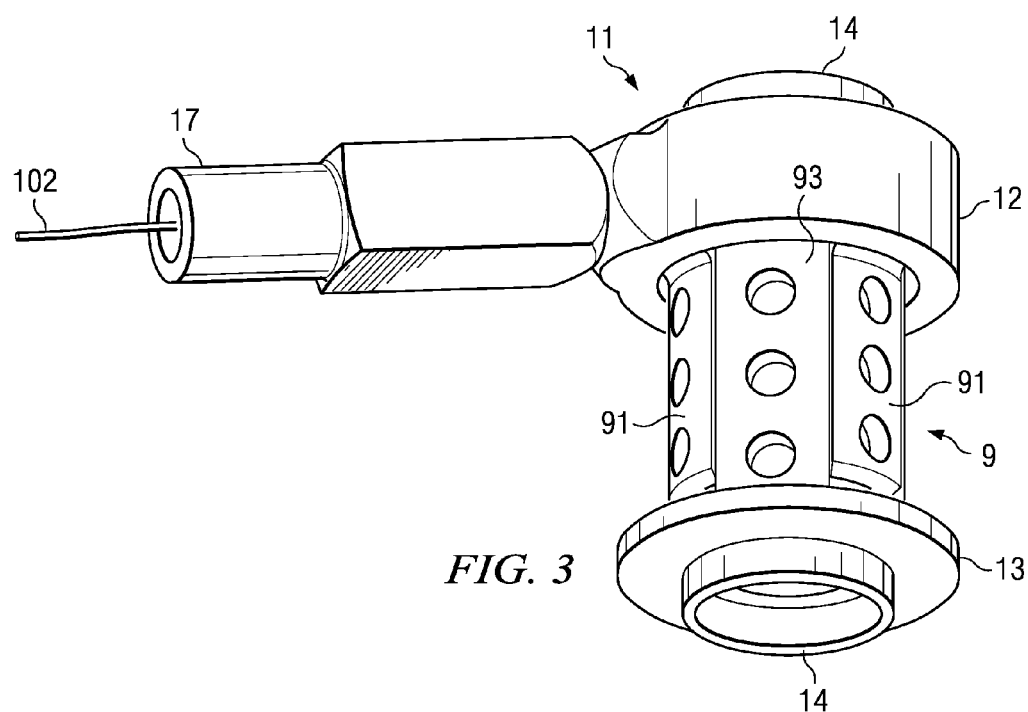
FIG. 3 is a perspective view of the expandable medical implant of FIG. 2 with a portion of the implant removed to illustrate internal components.
Figure 5:
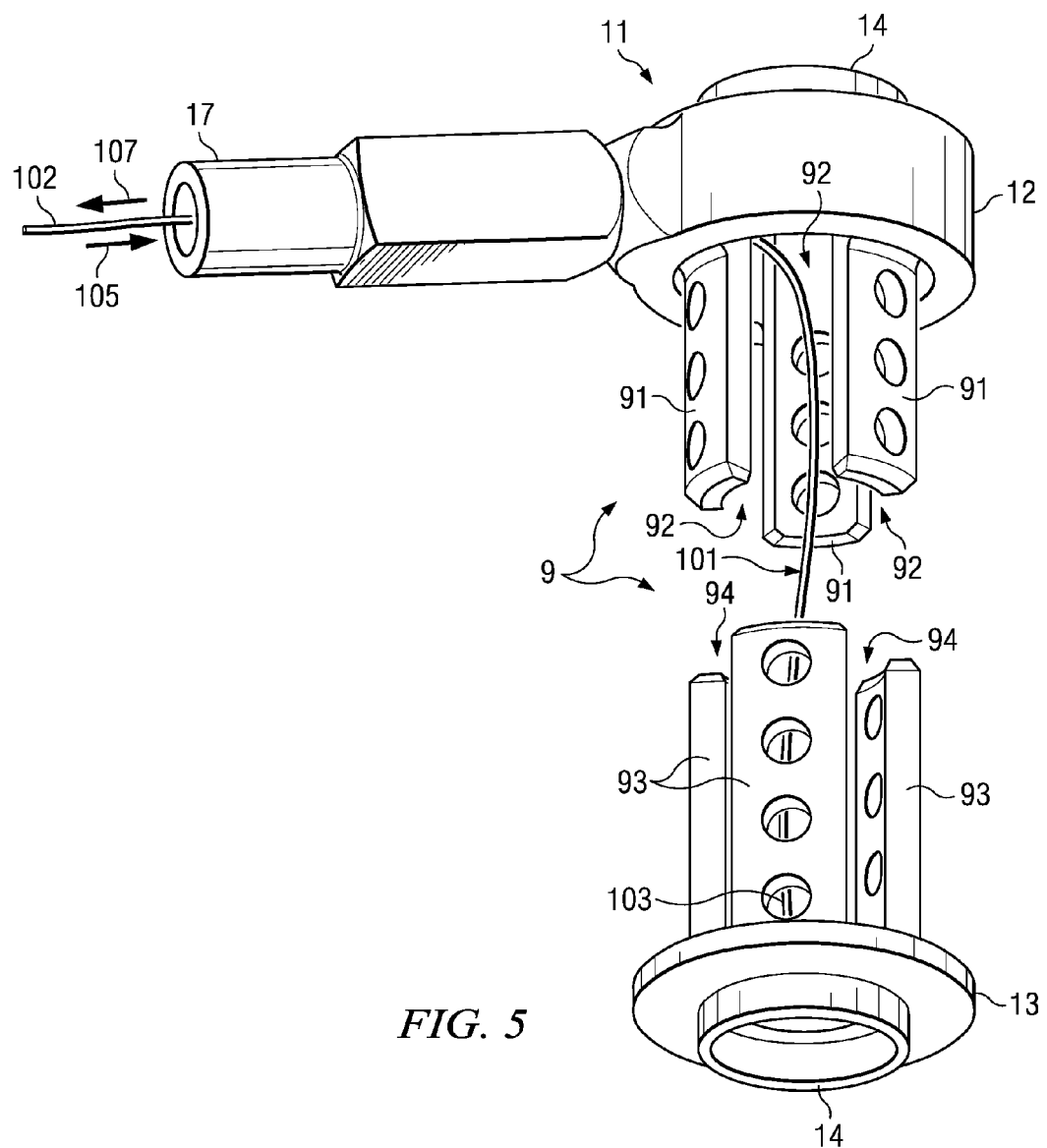
FIG. 5 is a perspective view of the expandable medical implant of FIG. 4 with a portion of the implant removed to illustrate internal components.

FIGS. 2-5 show components of a system for deploying an expandable medical implant 11. The expandable medical implant 11 includes a base 12 and an expandable end 13. The illustrated expandable medical implant 1 includes an expansion mechanism 16 (FIGS. 2 and 4) and a stabilizing structure 9 (FIGS. 3 and 5). The expansion mechanism 16 is removed from FIGS. 3 and 5 to clearly show the stabilizing structure 9. The expansion mechanism 16 shown is a bellows, but the expansion mechanism of other embodiments may be, without limitation, a telescoping mechanism, a ratchet mechanism, a threaded or partially threaded mechanism, or any other mechanism that may drive or hold expansion of an expandable medical implant. The embodiment of FIGS. 2-5 does not show a membrane such as the membrane 5 illustrated in FIG. 1, but other embodiments may include a membrane of a similar type in cooperation with the expandable medical implant 11.

The stabilizing structure 9 is illustrated in FIG. 3 with the expandable medical implant 11 in an unexpanded state, and in FIG. 5 with the expandable medical implant 11 in an expanded state. Superior fingers 91 are spaced apart to create superior channels 92 among the superior fingers 91. Inferior fingers 93 are spaced apart to create inferior channels 94 among the inferior fingers 93. In operation, the inferior fingers 93 slide in the superior channels 92, and the superior fingers 91 slide in the inferior channels 94 to maintain a substantially linear expansion of the expandable medical implant 1 while the base 12 and the expandable end 13 are moved toward or away from each other. In the embodiment shown, the stabilizing structure 9 is within the enclosed volume between the base and the expandable end. However, in other embodiments, the stabilizing structure may be outside of the enclosed volume.

The system for deploying an expandable medical implant 11 shown in FIGS. 2-5 includes an elongated member 101 with a distal end 103 and a proximal end 102 (FIG. 5). The illustrated distal end 103 is coupled to the expandable end 13 of the expandable medical implant 11. The elongated member 101 is in contact with the base 12 of the expandable medical implant 11 at least within the port 17 to provide a connection between the expandable end 13 and the base 12. The proximal end 102 extends from the expandable medical implant 11 through a port 17. The illustrated connection between the expandable end 13 and the base 12 with the elongated member 101 is a sliding connection because the elongated member 101 slides relative to the base 12 when the elongated member 101 is removed from or pushed into the port 17.

The proximal end 102 is configured to receive a force applied along its length. Arrow 105 shows the direction of a pushing or compressive force applied along the length of the elongated member 101 at its proximal end 102. Arrow 107 shows the direction of a pulling or tensile force applied along the length of the elongated member 101 at its proximal end 102. In other embodiments where the elongated member 101 is actuated by an alternative mechanism, the force applied to the elongated member 101 may be a twisting, winding, turning, or other effective force to push apart or pull together the base 12 and the expandable end 13. The character and function of the elongated member 101 is essentially similar to the character and function described in association with FIG. 1.

In some embodiments, elasticity in the material of the expansion mechanism 16 may serve as a biasing force to bias the expansion mechanism 16 toward an expanded or unexpanded state, as may be advantageous in various circumstances. The character and function of the expansion mechanism 16 and biasing of the expansion mechanism 16 are essentially similar to the character and function described in association with FIG. 1.

FIGS. 2-5 illustrate nozzles 14 extending from the expandable medical implant 11. The illustrated nozzles 14 are open to the interior of the expandable medical implant 11. In some embodiments, a balloon (not shown) may extend from an open, distal end of the nozzles 14. The balloon may be in fluid communication with the interior of the expandable medical implant 11. The nozzles 14 and balloons of some embodiments are configured to extend from expandable medical implant 11 and into an endplate of an adjacent vertebra. The balloons may be filled with a material, such as a flowable material, to assist in attachment of the expandable medical implant 11 to the adjacent vertebrae. One or both of the flowable material and the balloons may additionally have a therapeutic effect on the vertebrae. For example, and without limitation, the nozzles 14, the flowable material, and the balloons, alone or in combination, may help to stabilize the vertebrae. The flowable material passed through the nozzles 14 or used to inflate the balloons may be a curable material or may be a material that is used to expand the balloons, but does not cure in place. Once expanded, the balloons may also receive additional materials that permanently fill the balloons, or that have an additional therapeutic effect on the vertebrae. Any of the materials for use through the nozzles 14 or in the balloons may also be a fill material as described in detail below. In addition to the nozzles 14 or balloons, one or both ends of an embodiment of the expandable medical implant 11 my include teeth, spikes, ridges, indentations, roughening, knurling, or any other device for enhancing fixation between a vertebra and the expandable medical implant 11.

Figure 6:
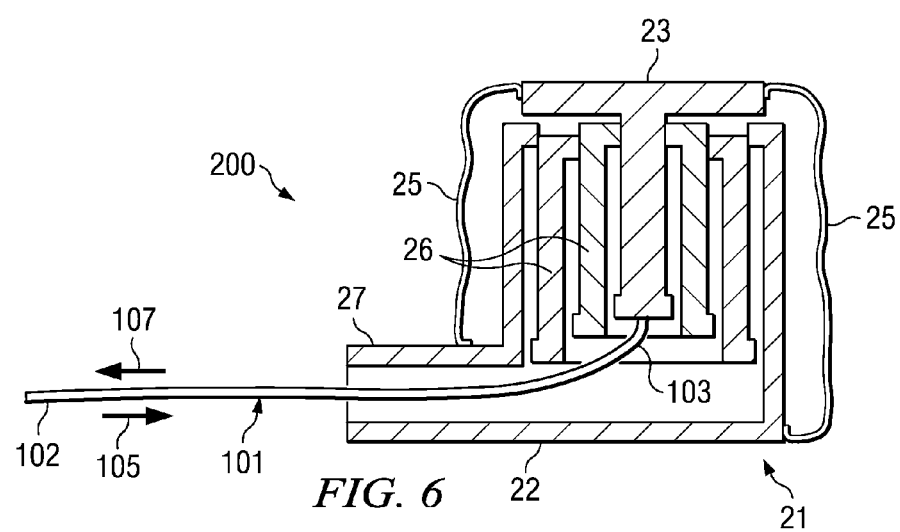
FIG. 6 is a cross-sectional view of an embodiment of a system for deploying an expandable medical implant in an unexpanded state.
Figure 4:
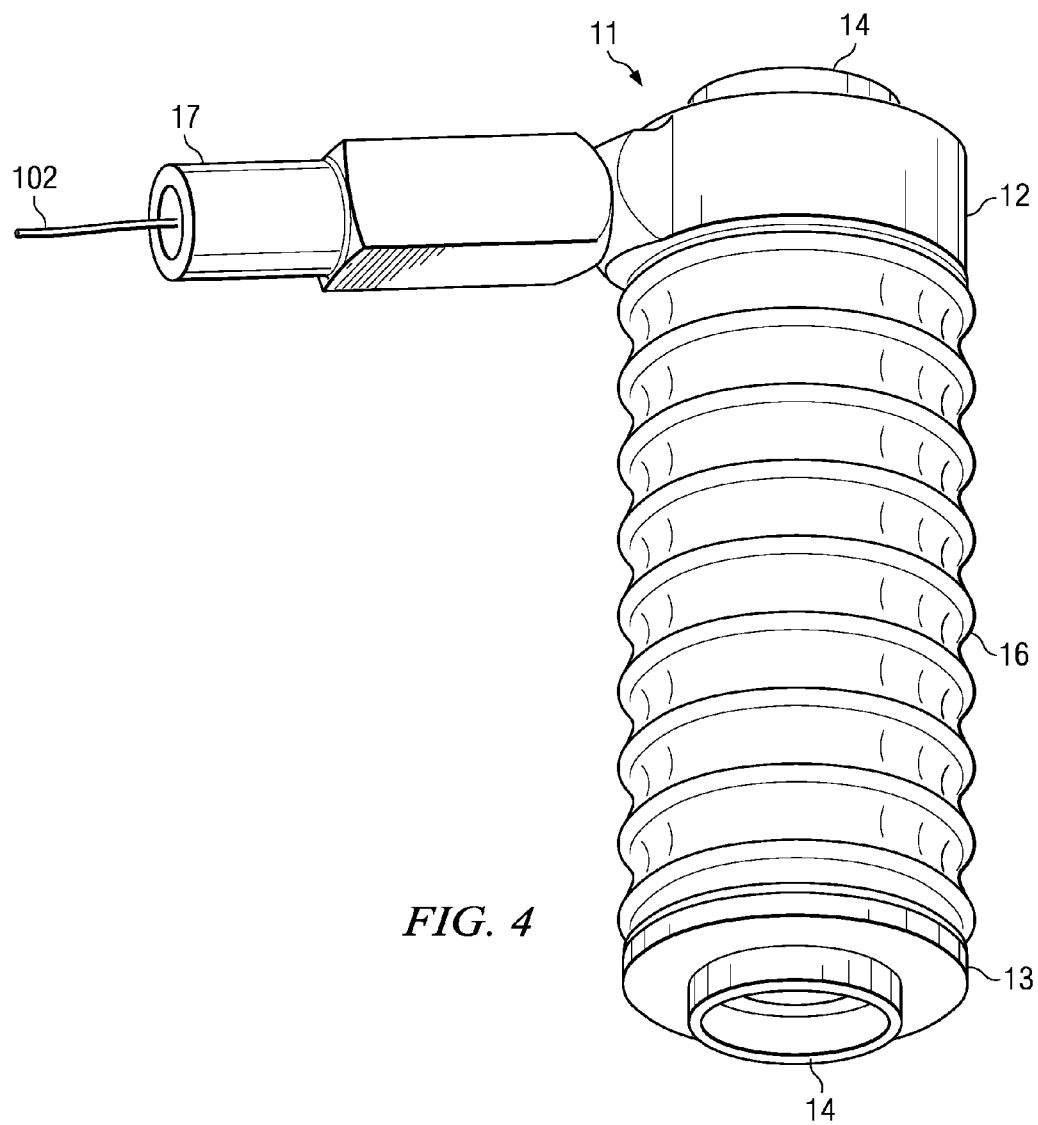
FIG. 4 is a perspective view of at least a portion of an expandable medical implant in an expanded state.
Figure 7:
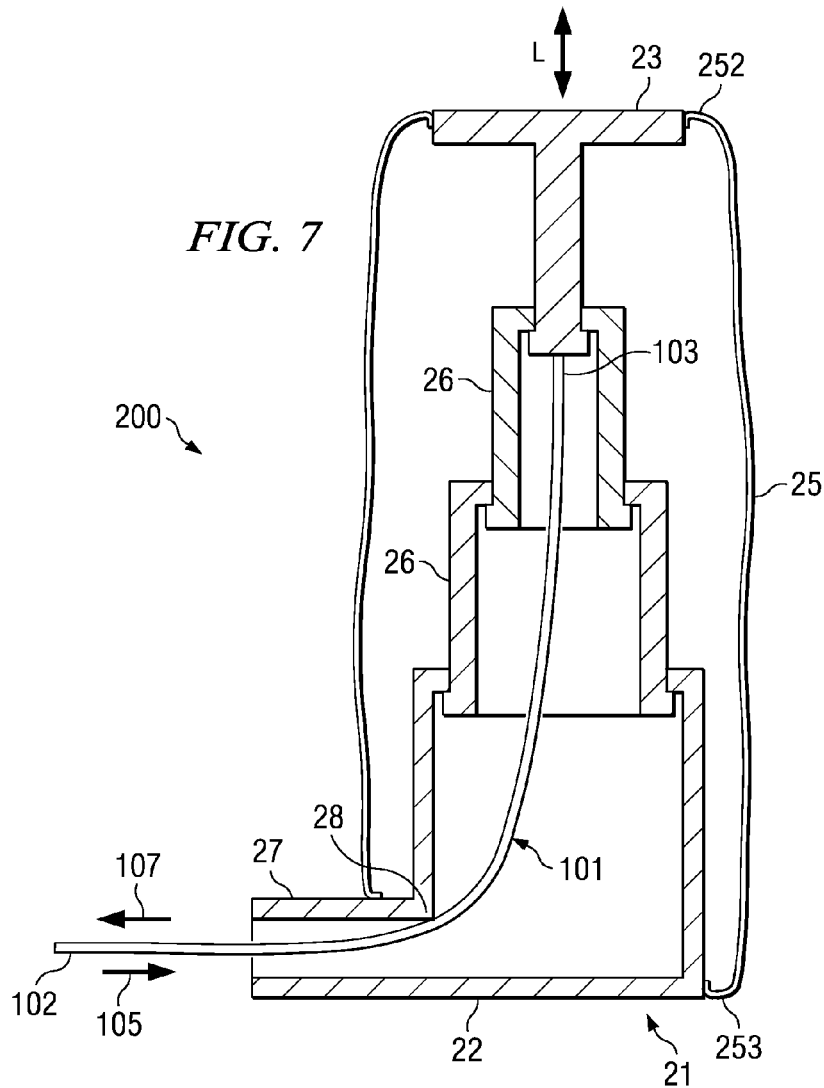
FIG. 7 is a cross-sectional view of the system for deploying an expandable medical implant of FIG. 6 in an expanded state.

FIGS. 6 and 7 illustrate a system 200 for deploying an expandable medical implant 21. The expandable medical implant 21 includes a base 22 and an expandable end 23. The illustrated expandable medical implant 21 includes a membrane 25 and telescoping cylinders 26. Rather than the telescoping cylinders 26 of the illustrated embodiment, other embodiments may be, without limitation, a bellows, a ratchet mechanism, a threaded or partially threaded mechanism, or any other mechanism that may drive or hold expansion of an expandable medical implant.

The telescoping cylinders 26 and membrane 25 are illustrated in an unexpanded state in FIG. 6, and in an expanded state in FIG. 7. The membrane 25 of some embodiments is configured to be placed between vertebrae and expanded such that an upper surface 252 contacts a first vertebra and an opposite lower surface 253 contacts a second vertebra to provide support between the vertebrae. The longitudinal axis, or linear expansion direction L, of the expandable medical implant 21 is illustrated in FIG. 7. Lateral expansion of the membrane 25 is also accomplished in some embodiments. As used herein, the term lateral means directions approximately normal to the linear expansion direction L.

The membrane 25 may be constructed, in whole or in part, of a non-permeable material or of a permeable material, which allows a certain amount of a fill material to pass through the membrane 25. The membrane 25 may include compliant or non-compliant balloon materials such as those commonly used to manufacture coronary and Kyphoplasty medical devices. These and other operable materials are essentially similar to the materials described in association with FIG. 1 above.

In the embodiment shown in FIGS. 6 and 7, telescoping cylinders 26 along with the base 22 and expandable end 23 define an enclosed volume. The membrane 25 defines an enclosed volume that incorporates the enclosed volume of the telescoping cylinders 26 along with the base 22 and expandable end 23. The enclosed volumes of both the telescoping cylinders 26 along with the base 22 and expandable end 23, and the membrane 25 are therefore volumes between the base 22 and the expandable end 23.

The system 200 for deploying an expandable medical implant 21 shown in FIGS. 6 and 7 includes an elongated member 101 with a distal end 103 and a proximal end 102. The illustrated distal end 103 is coupled to the expandable end 23 of the expandable medical implant 21. The elongated member 101 is in contact with the base 22 of the expandable medical implant 21 at a point 28 to provide a connection between the expandable end 23 and the base 22. The proximal end 102 extends from the expandable implant 21 in FIG. 7 through an opening or port 27. The illustrated connection between the expandable end 23 and the base 22 with the elongated member 101 is a sliding connection because the elongated member 101 slides relative to the base 22 when the elongated member is removed from or pushed into the port 27.

The proximal end 102 is configured to receive a force applied along its length. Arrow 105 shows the direction of a pushing or compressive force applied along the length of the elongated member 101 at its proximal end 102. Arrow 107 shows the direction of a pulling or tensile force applied along the length of the elongated member 101 at its proximal end 102. In other embodiments where the elongated member 101 is actuated by an alternative mechanism, the force applied to the elongated member 101 may be a twisting, winding, turning, or other effective force to push apart or pull together the base 22 and the expandable end 23. For example, and without limitation, the elongated member 101 may include threaded portions, turnbuckle portions, fasteners, or multiple members that move relative to one another to lengthen or shorten the elongated member 101. In some embodiments, the elongated member 101 is a wire, rod, or other relatively rigid device that is capable of transmitting both tensile and compressive forces to either or both pull together or push apart the base 22 and the expandable end 23. In other embodiments where it is only necessary to pull together the base 22 and the expandable end 23, the elongated member 101 may be a strand, string, rope, cable, or other member configured primarily to transmit tensile forces.

It may be advantageous to bias the telescoping cylinders 26 toward an unexpanded state to provide a low profile device for insertion. Other devices, such as but not limited to the elongated member 101, or a fluid injected through the port 27, may be used to expand the telescoping cylinders 26. A fluid that drives linear expansion of the expandable medical implant 21 or maintains linear expansion of the expandable medical implant 21 may be introduced through the port 27. The fluid may be merely for expansion and retention, or may be a component of a fill material intended to remain in the telescoping cylinders 26. As used in association with this function, a fluid may be a paste, gel, liquid, suspension, granular mixture, or similar substance. A substance as described herein will be considered a fluid even if it later cures or hardens to a non-fluidic state. Both the telescoping cylinders 26 and the membrane 25 may be unexpanded linearly. The port 27 may also be used to handle the expandable medical implant 21 or to guide the implant into a position where it can be effectively deployed.

In other circumstances, it may be preferred to bias the telescoping cylinders 26 toward an expanded state. With such an embodiment, another component, such as but not limited to the elongated member 101, may be used to keep the telescoping cylinders 26 in an unexpanded state while the expandable medical implant 21 is inserted. Following insertion, the telescoping cylinders 26 may be released and allowed to increase toward its expanded state by releasing the elongated member 101 relative to the base 22.

Figure 8:
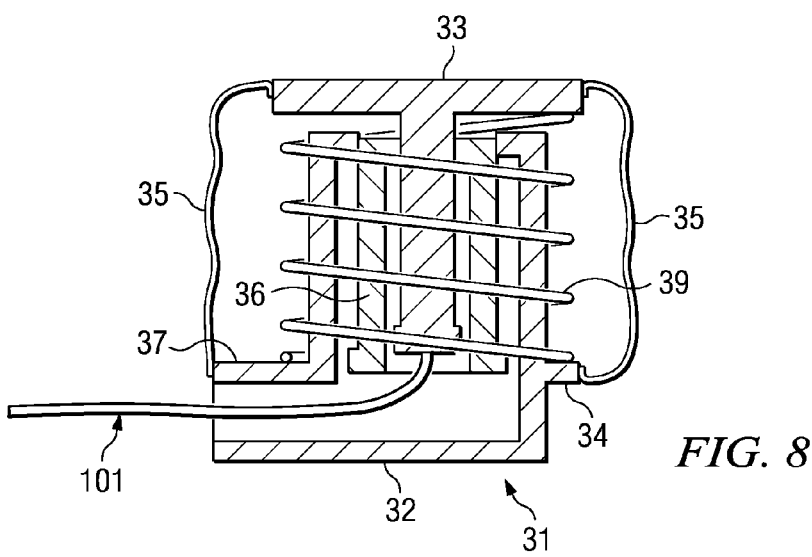
FIG. 8 is a cross-sectional view of an embodiment of a system for deploying an expandable medical implant in an unexpanded state, including an elevation view of a biasing member.
Figure 9:
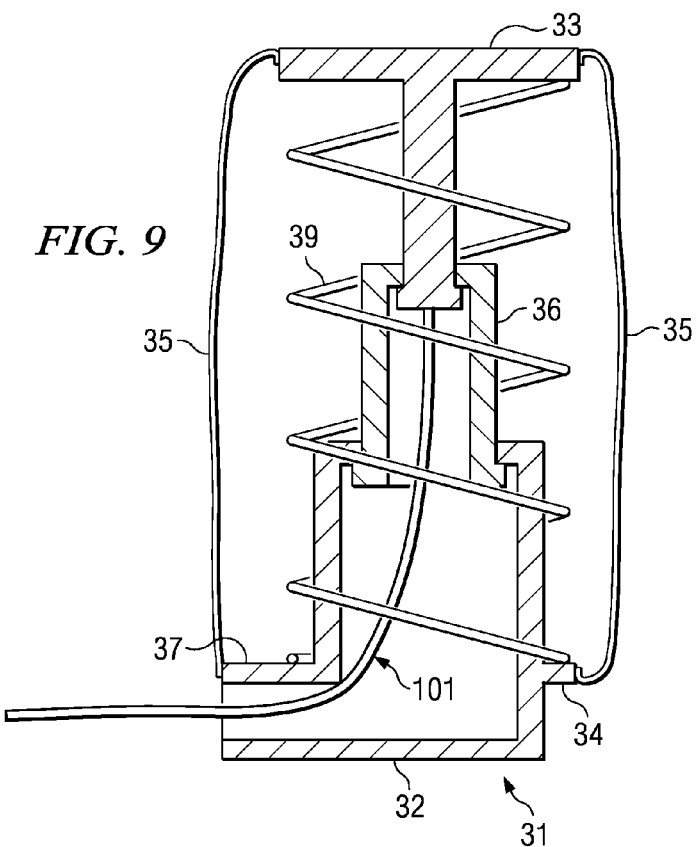
FIG. 9 is a cross-sectional view of the system for deploying an expandable medical implant of FIG. 8 in an expanded state, including an elevation view of a biasing member.

FIGS. 8 and 9 show a specific embodiment that also includes a spring 39 that may server as a biasing member to bias a telescoping cylinder 36 toward either an unexpanded or expanded state. The spring 39 is shown in elevation view, although the expandable medical implant 31 is shown in cross-sectional view. The embodiment of FIGS. 8 and 9 is similar to the embodiment of FIGS. 6 and 7, but includes the spring 39 to bias the telescoping cylinder 36, particular adaptations to accommodate the spring 39, and one telescoping cylinder 36 along with a base 32 and an expandable end 33, rather than two telescoping cylinders 26 as are shown in the embodiment of FIGS. 6 and 7.

The adaptations to accommodate the spring 39 include a shoulder 34 against which the spring 39 may push or pull, depending on whether the spring is biased toward an expanded or unexpanded state. It may be advantageous to bias the telescoping cylinder 36 toward an unexpanded state to automatically provide a low profile device for insertion. Other devices, such as but not limit to the elongated member 101, or a fluid injected through the port 37, may be used to expand the telescoping cylinder 36. A fluid that drives linear expansion of the expandable medical implant 31 or maintains linear expansion of the expandable medical implant 31 may be introduced through the port 37. The fluid may be merely for expansion and retention, or may be a component of a fill material intended to remain in the telescoping cylinder 36. As used in association with this function, a fluid may be a paste, gel, liquid, suspension, granular mixture, or similar substance. A substance as described herein will be considered a fluid even if it later cures or hardens to a non-fluidic state. Both the telescoping cylinder 36 and the membrane 35 may be initially unexpanded linearly. The port 37 may also be used to handle the expandable medical implant 31 or to guide the implant into a position where it can be effectively deployed.

In other circumstances, it may be preferred to bias the telescoping cylinder 36 toward an expanded state. With such an embodiment, another component, such as but not limit to the elongated member 101, may be used to keep the telescoping cylinder 36 in an unexpanded state while the expandable medical implant 31 is inserted. Following insertion, the telescoping cylinder 36 may be released and allowed to increase toward its expanded state by releasing the elongated member 101 relative to the base 32.

Figure 10:
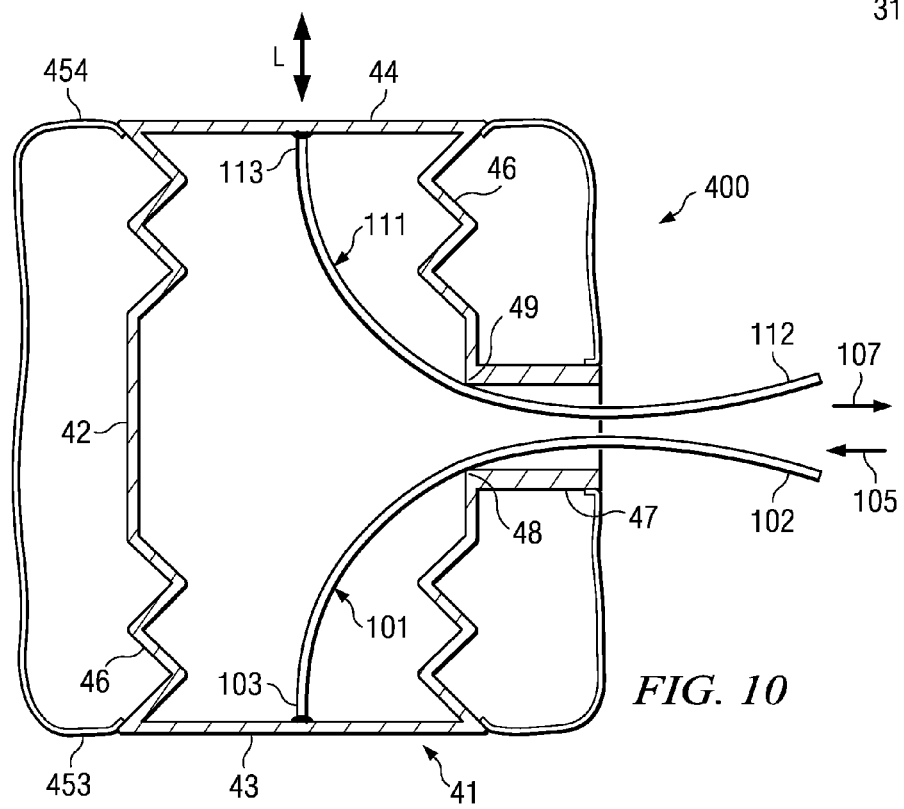
FIG. 10 is a cross-sectional view of an embodiment of a system for deploying an expandable medical implant in a partially expanded state.

FIG. 10 illustrates a system 400 for deploying an expandable medical implant 41. The expandable medical implant 41 includes a base 42, an expandable end 43, and an opposite expandable end 44 that extends from the base 42 in a direction opposite from the expandable end 43. The illustrated expandable medical implant 41 includes a membrane 45 and an expansion mechanism 46. The expansion mechanism 46 shown in FIG. 10 is a pair of bellows that extend in two directions away from the base 42. The expansion mechanism of other embodiments may be, without limitation, a combination of nested, telescoping cylinders, a ratchet mechanism, a threaded or partially threaded mechanism, or any other mechanism that may drive or hold expansion of an expandable medical implant.

The membrane 45 is illustrated in a partially expanded configuration in FIG. 10. The membrane 45 of some embodiments is configured to be placed between vertebrae and expanded such that an upper surface 454 contacts a first vertebra and an opposite lower surface 453 contacts a second vertebra to provide support between the vertebrae. The longitudinal axis, or linear expansion direction L, of the expandable medical implant 41 is illustrated in FIG. 10. Lateral expansion of the membrane 45 is also accomplished in some embodiments. As used herein, the term lateral means directions approximately normal to the linear expansion direction L.

The membrane 45 may be constructed, in whole or in part, of a non-permeable material or of a permeable material, which allows a certain amount of a fill material to pass through the membrane 45. The membrane 45 may include compliant or non-compliant balloon materials such as those commonly used to manufacture coronary and Kyphoplasty medical devices. These and other operable materials are essentially similar to the materials described in association with FIG. 1 above.

In the embodiment shown in FIG. 10, the expansion mechanism 46 defines an enclosed volume, and the membrane 45 defines an enclosed volume that incorporates the enclosed volume of the expansion mechanism 46. The enclosed volumes of both the expansion mechanism 46 and the membrane 45 are therefore volumes between the base 42 and the expandable end 43.

The system 400 for deploying an expandable medical implant 41 shown in FIG. 10 includes an elongated member 101 with a distal end 103 and a proximal end 102. The illustrated distal end 103 is coupled to the expandable end 43 of the expandable medical implant 41. The elongated member 101 is in contact with the base 42 of the expandable medical implant 41 at a point 48 to provide a connection between the expandable end 43 and the base 42. The proximal end 102 extends from the expandable implant 41 in FIG. 10 through an opening or port 47. The illustrated connection between the expandable end 43 and the base 42 with the elongated member 101 is a sliding connection because the elongated member 101 slides relative to the base 42 when the elongated member is removed from or pushed into the port 47. The expandable medical implant 41 shown in FIG. 10 additionally includes an opposite elongated member 111 with a distal end 113 and a proximal end 112. The illustrated distal end 113 is coupled to the opposite expandable end 44 of the expandable medical implant 41. The opposite elongated member 111 is in contact with the base 42 of the expandable medical implant 41 at a point 49 to provide a connection between the opposite expandable end 44 and the base 42. The proximal end 112 extends from the expandable implant 41 in FIG. 10 through the port 47. The illustrated connection between the opposite expandable end 44 and the base 42 with the opposite elongated member 111 is a sliding connection because the opposite elongated member 111 slides relative to the base 42 when the elongated member is removed from or pushed into the port 47.

The proximal end 112 of the illustrated embodiment is configured to receive a force applied along its length. Arrow 105 shows the direction of a pushing or compressive force applied along the length of the elongated member 111 at its proximal end 112. Arrow 107 shows the direction of a pulling or tensile force applied along the length of the elongated member 111 at its proximal end 112. In other embodiments where the opposite elongated member 111 is actuated by an alternative mechanism, the force applied to the opposite elongated member 111 may be a twisting, winding, turning, or other effective force to push apart or pull together the base 42 and the opposite expandable end 44. For example, and without limitation, the opposite elongated member 111 may include threaded portions, turnbuckle portions, fasteners, or multiple members that move relative to one another to lengthen or shorten the opposite elongated member 111. In some embodiments, the opposite elongated member 111 is a wire, rod, or other relatively rigid device that is capable of transmitting both tensile and compressive forces to either or both pull together or push apart the base 42 and the opposite expandable end 44. In other embodiments where it is only necessary to pull together the base 42 and the opposite expandable end 44, the elongated member 111 may be a strand, string, rope, cable, or other member configured primarily to transmit tensile forces.

In some embodiments, the elongated member 101 and the opposite elongate member 111 may be, in whole or in part, joined along their lengths. In some embodiments, the joining is near their respective proximal ends 102, 112. In this configuration, operation of the elongated member 101 and opposite elongated member 111 may be accomplished by a common application of a pushing or pulling force to the joined elongated members 101, 111.

In some embodiments, elasticity in the material of the expansion mechanism 46 may sever as a biasing force to bias the expansion mechanism 46 toward an expanded or unexpanded state, as may be advantageous in various circumstances. For example, it may be advantageous to bias the expansion mechanism 46 toward an unexpanded state to provide a low profile device for insertion. Other devices, such as but not limit to the elongated member 101, the opposite elongated member 111, or a fluid injected through the port 47, may be used to expand the expansion mechanism 46. A fluid that drives linear expansion of the expandable medical implant 41 or maintains linear expansion of the expandable medical implant 41 may be introduced through the port 47. The fluid may be merely for expansion and retention, or may be a component of a fill material intended to remain in the expansion mechanism 46. As used in association with this function, a fluid may be a paste, gel, liquid, suspension, granular mixture, or similar substance. A substance as described herein will be considered a fluid even if it later cures or hardens to a non-fluidic state. Both the expansion mechanism 46 and the membrane 45 may initially be unexpanded linearly. The port 47 may also be used to handle the expandable medical implant 41 or to guide the implant into a position where it can be effectively deployed.

In other circumstances, it may be preferred to bias the expansion mechanism 46 toward an expanded state. With such an embodiment, another component, such as but not limit to the elongated member 101 and the opposite elongated member 111, may be used to keep the expansion mechanism 46 in an unexpanded state while the expandable medical implant 41 is inserted. Following insertion, the expansion mechanism 46 may be released and allowed to increase toward its expanded state by releasing one or both of the elongated member 101 and the opposite elongated member relative to the base 2.

As shown in FIGS. 2-5, the cross-sectional shape of some embodiments of the expandable medical implant 11 is substantially circular. However, the cross-sectional shape of any of the expandable medical implants may be any functional shape, such as but not limited to, generally oval, rectangular, triangular, polygonal, concave-convex, or combinations of these shapes.

In any of the embodiments of FIGS. 1-10, the expansion mechanisms, bases, expandable ends, telescoping cylinders, or other components that interact with the membranes, may include one or more transfer openings from a component to an interior of the membranes. In some embodiments, the transfer opening is a hole through which a fluid or fill material, or both, may pass. Fluid, fill material, or both may enter the respective expandable medical implants through the ports 7, 17, 27, 37, 47 and pass through one or more transfer openings and into the membrane. In some embodiments, a valve is provided at the transfer opening to control flow to the membrane. The valve may be controlled by direct manipulation or through instrumentation connected through the port 7, 17, 27, 37, 47.

Fill material may enter the expandable medical implant as a fluid, and then harden or cure in the implant. In some embodiments, a non-hardenable and non-curing fluid is used to expand, or to hold expansion in, the implant or one or some of the components of the implant. A fill material may then be introduced into at least the membrane 5, 25, 35, 45 to provide support between an upper surface and lower surface of the membrane. The fill material may be a paste, gel, liquid, suspension, granular mixture, or similar substance. Non-limiting examples of fill materials include bone cement, paste, morselized allograft, autograft, or xenograft bone, ceramics, or various polymers. An example bone cement is polymethylmethacrylate (PMMA), which may be made from methylmethacrylate, polymethylmethacrylate, esters of methacrylic acid, or copolymers containing polymethylmethacrylate and polystyrene. Additional non-limiting examples of the fill material include semi-rigid flowable or hardenable material such as silicone or various types of urethane materials. It should further be understood that other types of fill materials which are not necessarily hardenable or curable may be used in association with the present invention. For example, the fill material may comprise beads or small particles or grains of material, some of which may, in aggregate, achieve a harder consistency as a result of interlocking or compaction. In some embodiments, the fill material may also include a bone growth promoting substance. Osteogenic or bone growth promoting substances may include, without limitation, autograft, allograft, xenograft, demineralized bone, synthetic and natural bone graft substitutes, such as bioceramics and polymers, and osteoinductive factors. A separate carrier to hold materials within the device may also be used. These carriers may include collagen-based carriers, bioceramic materials, such as BIOGLASS®, hydroxyapatite and calcium phosphate compositions. The carrier material may be provided in the form of a sponge, a block, folded sheet, putty, paste, graft material or other suitable form. The osteogenic compositions may include an effective amount of a bone morphogenetic protein (BMP), transforming growth factor β1, insulin-like growth factor, platelet-derived growth factor, fibroblast growth factor, LIM mineralization protein (LMP), and combinations thereof or other therapeutic or infection resistant agents, separately or held within a suitable carrier material. Introduction of fluid or fill material into an expandable medical implant embodiment may be through a syringe or similar device, through direct placement, or by any other effective mechanism.

Each of the embodiments disclosed herein may be described as a system for deploying an expandable medical implant. The system includes an expandable medical implant with a base and an expandable end and an enclosed volume between the base and the expandable end. The system also includes a means for pushing apart or pulling together the base and the expandable end.

Embodiments of the implant in whole or in part may be constructed of biocompatible materials of various types. Examples of implant materials include, but are not limited to, non-reinforced polymers, carbon-reinforced polymer composites, PEEK and PEEK composites, low density polyethylene, shape-memory alloys, titanium, titanium alloys, cobalt chrome alloys, stainless steel, ceramics and combinations thereof. If a trial instrument or implant is made from radiolucent material, radiographic markers can be located on the trial instrument or implant to provide the ability to monitor and determine radiographically or fluoroscopically the location of the body in the spinal space. In some embodiments, the implant or individual components of the implant may be constructed of solid sections of bone or other tissues. Tissue materials include, but are not limited to, synthetic or natural autograft, allograft or xenograft, and may be resorbable or non-resorbable in nature. Examples of other tissue materials include, but are not limited to, hard tissues, connective tissues, demineralized bone matrix and combinations thereof.

Some embodiments may also include supplemental fixation devices in addition to or as part of the expandable medical implant for further stabilizing the anatomy. For example, and without limitation, rod and screw fixation systems, anterior, posterior, or lateral plating systems, facet stabilization systems, spinal process stabilization systems, and any devices that supplement stabilization may be used as a part of or in combination with the expandable medical implant.

An embodiment of the invention is a method of implanting an expandable medical implant. The method embodiment includes providing the expandable medical implant with a base and an expandable end and an enclosed volume between the base and the expandable end. The expandable medical implant may also include an elongated member with a distal end and a proximal end. The distal end is coupled to the expandable end of the expandable medical implant and the elongated member is in contact with the base of the expandable medical implant. The method may also include introducing the expandable medical implant through an incision in a patient. Introduction through an incision of some embodiments is conducted while the expandable medical implant is an unexpanded or less than fully expanded state. Consequently, a smaller, less invasive incision is possible.

Method embodiments of the invention may also include applying a compressive force to the elongated member to push apart the base and the expandable end of the expandable medical implant. The base and the expandable end may be pushed apart partially or temporarily to properly locate the expandable medical implant while imaging or alignment procedures are accomplished. For example, and without limitation, portions of the base and the expandable end may be pressed against vertebrae on one or both sides of the expandable medical implant. If proper alignment is confirmed, the expandable medical implant may be secured in place. If proper alignment is not achieved, tensile force may be applied to the elongated member, or compressive force released, to reduce the expansion of the expandable medical implant while the expandable medical implant is repositioned or removed.

Another method embodiment includes providing the expandable medical implant with a base and an expandable end and an enclosed volume between the base and the expandable end. The expandable medical implant may also include an elongated member with a distal end and a proximal end. The distal end is coupled to the expandable end of the expandable medical implant and the elongated member is in contact with the base of the expandable medical implant. Method embodiments of the invention may also include applying a tensile force to the elongated member to pull together the base and the expandable end of the expandable medical implant. The method may additionally include introducing the expandable medical implant through an incision in a patient. Introduction through an incision of some embodiments is conducted while the expandable medical implant is an unexpanded or less than fully expanded state. Consequently, a smaller, less invasive incision is possible.

The tensile force on the elongated member may be released to allow the base and the expandable end of the expandable medical implant to separate. In some embodiments, elasticity in components of the expandable medical implant, or a separate biasing member, may be included with the expandable medical implant to urge the base away from the expandable end. The base and the expandable end may be allowed to expand partially or temporarily to properly locate the expandable medical implant while imaging or alignment procedures are accomplished. For example, and without limitation, portions of the base and the expandable end may be pressed against vertebrae on both sides of the expandable medical implant. If proper alignment is confirmed, the expandable medical implant may be secured in place. If proper alignment is not achieved, tensile force may be applied to the elongated member to reduce the expansion of the expandable medical implant while the expandable medical implant is repositioned or removed.

A fill material may be introduced into the enclosed volume between the base and the expandable end of some embodiments. The fill material may serve as a supplement to mechanisms of the expandable medical implant that otherwise secure the implant in place, or the fill material may be a primary component to secure the expandable medical implant in place. The fill material may occupy only a portion of the volume between the base and the expandable end, or it may be used to further expand portions of the expandable medical implant such as the membrane 5, 25, 35, 45, one or both linearly and laterally.

Some portion of the elongated member may extend from the expandable medical implant after the expandable medical implant is secured in place. Therefore, an additional act of some methods embodiments is to remove at least a portion of the elongated member from the expandable medical implant. The elongated member may be cut or twisted off with an instrument, released from its connection to the expandable end of the implant. The elongated member may, at any position along its length, include a release mechanism, portion of reduced strength, or other characteristic that facilitates removal of all or a portion of the elongated member.

The expandable medical implant shown in FIGS. 1-10 presents a small profile in its unexpanded state so that it is well-suited for implantation from a generally posterior approach. However, embodiments of the invention may include implantation from any surgical approach, including but not limited to, posterior, lateral, anterior, transpedicular, lateral extracavitary, in conjunction with a laminectomy, in conjunction with a costotransversectomy, or by any combination of these and other approaches.

Various method embodiments of the invention are described herein with reference to particular expandable medical implants. However, in some circumstances, each disclosed method embodiment may be applicable to each of the expandable medical implants, or to some other implant operable as disclosed with regard to the various method embodiments.

Terms such as lower, upper, anterior, posterior, inferior, superior, lateral, medial, contralateral, and the like have been used herein to note relative positions. However, such terms are not limited to specific coordinate orientations, but are used to describe relative positions referencing particular embodiments. Such terms are not generally limiting to the scope of the claims made herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A system for deploying an expandable medical implant comprising:
   an expandable medical implant with a base and an expandable end and an enclosed volume between the base and the expandable end;
   an elongated member with a distal end and a proximal end wherein the distal end is coupled to the expandable end of the expandable medical implant, and the elongated member is in contact with the base of the expandable medical implant to provide a connection between the expandable end and the base, and wherein the proximal end extends from the expandable implant and the proximal end is configured to receive a force applied along its length; and
   a stabilizing structure to maintain a substantially linear expansion of the expandable medical implant while the base and the expandable end are moved toward or away from each other, the stabilizing structure comprising:
   a first channel coupled with the base; and
   a second channel coupled with the expandable end,
   wherein the first channel interdigitates with a portion of the expandable end and the second channel interdigitates with a portion of the base.

2. The system of claim 1 wherein the base of the expandable medical implant is configured to couple with a vertebral endplate and the expandable end of the expandable medical implant is configured to couple with an opposite vertebral endplate.

3. The system of claim 1 wherein the elongated member passes through an opening in the base of the expandable medical implant, through the enclosed volume, and couples with the expandable end of the expandable medical implant.

4. The system of claim 1 wherein the elongated member is a wire configured to transmit tensile and compressive forces.

5. The system of claim 1 wherein the elongated member is a strand configured to transmit tensile forces.

6. The system of claim 1 wherein the connection between the base and the expandable end is a sliding connection along the elongated member.

7. The system of claim 1 wherein the expandable medical implant is made with a bias that pushes apart the base and the expandable end of the expandable medical implant.

8. The system of claim 1 wherein the expandable medical implant is made with a bias that pulls together the base and the expandable end of the expandable medical implant.

9. The system of claim 1, further comprising a biasing member.

10. The system of claim 9 wherein the biasing member is a spring configured to push apart the base and the expandable end of the expandable medical implant.

11. The system of claim 9 wherein the biasing member is a spring configured to pull together the base and the expandable end of the expandable medical implant.

12. The system of claim 1, further comprising a fill material for introduction into the volume between the base and the expandable end of the expandable medical implant.

13. The system of claim 1 wherein the stabilizing structure is within the enclosed volume.

* * * * *